(12) United States Patent
Veverka et al.

(10) Patent No.: US 7,868,180 B2
(45) Date of Patent: Jan. 11, 2011

(54) PROCESS FOR THE PREPARATION OF SARTAN DERIVATIVES AND INTERMEDIATES USEFUL IN SUCH PROCESS

(75) Inventors: Miroslav Veverka, Bratislava (SK); Martin Putala, Bratislava (SK); Heinrich Brath, Hostova (SK); Silvo Zuppancic, Novo Mesto (SI)

(73) Assignee: KRKA, d.d. Novo mesto, Novo Mesto (SI)

( * ) Notice: Subject to any disclaimer, the term of this patent is extended or adjusted under 35 U.S.C. 154(b) by 137 days.

(21) Appl. No.: 12/067,612

(22) PCT Filed: Sep. 20, 2006

(86) PCT No.: PCT/EP2006/009159

§ 371 (c)(1),
(2), (4) Date: Aug. 15, 2008

(87) PCT Pub. No.: WO2007/039117

PCT Pub. Date: Apr. 12, 2007

(65) Prior Publication Data

US 2008/0312451 A1  Dec. 18, 2008

(30) Foreign Application Priority Data

Sep. 20, 2005   (EP)   ................................. 05020493

(51) Int. Cl.
C07D 233/00   (2006.01)
C07D 249/00   (2006.01)

(52) U.S. Cl. .................................. 548/262.2; 548/300.1

(58) Field of Classification Search .............. 548/262.2, 548/300.1
See application file for complete search history.

(56) References Cited

U.S. PATENT DOCUMENTS

| 5,128,356 A | 7/1992 | Naka et al. |
| 5,243,054 A | 9/1993 | Naka et al. |

FOREIGN PATENT DOCUMENTS

| CN | 1164587 | 11/1997 |
| EP | 0578125 | 1/1994 |
| EP | 0796852 | 9/1997 |
| EP | 1533305 | 5/2005 |
| WO | WO-9938847 | 8/1999 |
| WO | WO-2004065383 | 8/2004 |
| WO | WO-2005051929 | 6/2005 |
| WO | WO-2005113518 | 12/2005 |
| WO | WO-2006089927 | 8/2006 |

OTHER PUBLICATIONS

Larsen, et al., J. Org. Chem., 1994, 59, 6391.*
Larsen et al., JOC, 1994, vol. 59, p. 6391.*
Database CAPLUS Abstract, Accession No. 2003:759274.
Larsen, R.D. et al.,"Efficient Synthesis of Losartan, A Nonpeptide Angiotensin II Receptor Antagonist," Journal of Organic Chemistry, vol. 59(21):6391-6394 (1994).
Sumalatha, B.S.Y. et al., "Improved Synthesis of Irbesartan, An Antihypertensive Active Pharmaceutical Ingredient," Synthetic Communications, vol. 35(14):1979-1982 (2005).
International Search Report for Application No. PCT/EP2006/009159, dated Aug. 5, 2007.
International Preliminary Report on Patentability for Application No. PCT/EP2006/009159, dated Nov. 2, 2008.

* cited by examiner

Primary Examiner—Susannah Chung
(74) Attorney, Agent, or Firm—McCarter & English, LLP

(57) ABSTRACT

The invention provides a process for the preparation of a sartan derivative of formula (I) (formula as filed in paper form) (I) wherein the substituents have the meaning indicated in the description, or a pharmaceutically acceptable salt thereof, comprising reacting 2-cyanophenylboronic acid or a derivative thereof with a p-halobenzyl-1H-imidazole derivative of formula (VI), (formula as filed in paper form) (VI) wherein (part of formula as filed in paper form), X, Y, $R_1$ and $R_2$ are as defined above, and Z is I, Br or Cl, in the presence of a transition metal catalyst and an inorganic or organic base. The invention also provides new intermediates of formula (V), (formula as filed in paper form) (V) wherein M is an alkali metal or an $NR_4R_5R_6R_7$ group; and of formula (II) (formula as filed in paper form) (II).

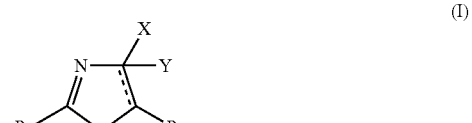

(I)

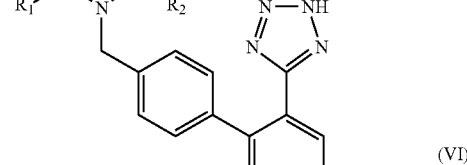

(VI)

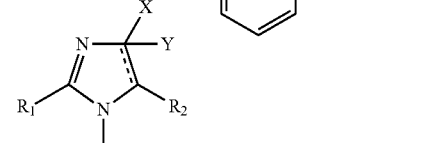

(V)

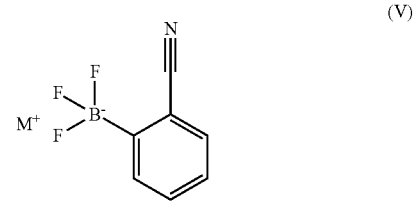

15 Claims, No Drawings

PROCESS FOR THE PREPARATION OF SARTAN DERIVATIVES AND INTERMEDIATES USEFUL IN SUCH PROCESS

RELATED APPLICATIONS

This application is a 35 U.S.C. 371 national stage filing of International Application No. PCT/EP2006/009159, filed Sep. 20, 2006, which claims priority to European Patent Application No. 05 020 493.2, filed Sep. 20, 2005. The contents of these applications are hereby incorporated by reference in their entireties.

FIELD OF THE INVENTION

The present invention relates to a process for the preparation of substituted biphenyl imidazole compounds as useful intermediates in the synthesis of certain sartan derivatives that are angiotensin II receptors, in particularly losartan, olmesartan medoxomil, candesartan cilexetil and irbesartan.

Angiotensin II receptors, such as losartan, olmesartan medoxomil (EP 0 503 785; EP 0 545 912), candesartan cilexetil (EP 0 459 136; EP 0 720 982), and irbesartan (EP 0 454 511) are effective inhibitors for angiotensin-converting enzymes and are used for the treatment of hypertension, renal failure and glaucoma. A number of non-peptide analogs have been reported to have angiotensin II receptor properties (U.S. Pat. No. 4,355,040, Wong P. C., J. Pharm. Exp. Ther., 1990, 255 (2), 584). The majority of angiotensin II receptors have as a common structural feature a biphenyl moiety with a heterocycle in the 4-position. For example losartan has the following formula

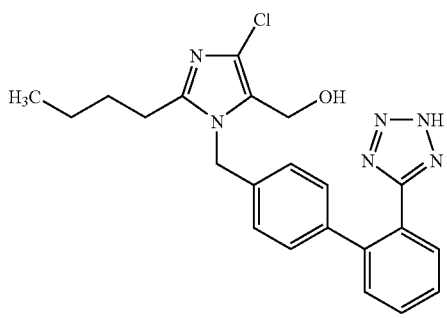

In the context of this invention, the term "losartan", also includes pharmaceutically acceptable hydrates and solvates of a compound having formula (I). The same applies to the other sartan derivatives mentioned in this application.

BACKGROUND OF THE INVENTION

Various approaches are known which describe the synthesis of substituted biphenyl imidazole compounds, which are useful in the synthesis of 1,2,4,5-substituted imidazoles, representing valuable intermediates in the synthesis of losartan.

Losartan potassium, being the first compound of a new class of drugs, was obtained, in a key step, via a heterogeneous Suzuki cross-coupling between trityltetrazole phenylboronic acid and 1-(4-bromobenzyl)-2-n-butyl-4-chloro-1H-imidazole-5-yl derivative (Larsen D. R., et al. J. Org. Chem. 1994, 59, 6391, U.S. Pat. No. 5,130,439, U.S. Pat. No. 5,310, 928).

Larsen D. R., J. Org. Chem. 1994, 59, 6391 discloses a process of direct N-alkylation of 1H-imidazole derivatives to obtain a benzylated imidazole. This compound is reacted with a trityl-protected phenyltetrazole boronic acid via a Suzuki cross-coupling to give a losartan.

U.S. Pat. No. 5,310,928 discloses novel tetrazolylphenyl-boronic acids and their derivatives, methods for their preparation and their use in processes for the preparation of angiotensin II receptor antagonists via Suzuki cross-coupling reactions. Both Larson and U.S. Pat. No. 5,310,928 require the protection of the nitrogen atom at position 2 of the tetrazole moiety, since the unprotected tetrazole contaminates the catalyst [Smith, G. B.; Dezeny, G: C.; Hughes, D. L.; King, A. O.; Verhoeven, T. R. J. Org. Chem. 1994, 59, 8151.]. The protection of the tetrazole moiety is usually carried out by a trityl group [a) Larsen, R. D.; King, A. O.; Chen, C.; Y.; Corley, E. G.; Foster, B. S.; Roberts, F. E.; Yang, C.; Lieberman, D. R.; Remwr, R. A.; Tschaen, D. M.; Verhoeven, T. R.; Reider, P. J. J. Org. Chem. 1994, 59, 6391. b) PCT Int. Appl., 9310106, 1993. c) Ger. Offen., 4313747, 1994.]. However, this methodology is not very effective, since the trityl group is quite labile and even traces of destrityl tetrazole boronic acid lower the yield of cross-coupling product significantly [Smith, G. B.; Dezeny, G: C.; Hughes, D. L.; King, A. O.; Verhoeven, T. R. J. Org. Chem. 1994, 59, 8151.].

A common method for the preparation of a tetrazole moiety is the transformation of a cyano group. Hird, M., J.C.S. Perkin. Trans. I. 1998, 20, 3479, Norman H. M., J. Med. Chem. 1995, 38, describe a Suzuki-Miyaura reaction wherein 2-bromobenzonitrile is used as an electrophile for the construction of 2-cyanobiphenyl. However, the problem of 2-cyanophenylboronic acid itself is its low stability, as it undergoes exothermic decomposition especially at temperatures over 90° C. [Urawa, Y.; Naka, H.; Miyazawa, M.; Souda, S.; Ogura, K. J. Organomet. Chem. 2002, 653, 269.]. Therefore, only few reports are available, describing the use of 2-cyanophenylboronic acid for cross-coupling reactions to give 2-cyanobiphenyl compounds in moderate yields (45-67%) [a) Thomas, A. P. et al., Bioorg. Med. Chem. Lett. 1994, 4, 2615; b) Yang, G. X. et al., Bioorg. Med. Chem. Lett. 2002, 12, 1497; c) Wu, T. Y. H. et al. Org. Lett. 2001, 3, 3827]. General methods for the preparation, properties and use of boronic acids and derivatives are summarized in "Metal-Organic Compounds", Advances in Chemistry Series, No. 23, American Chemical Society, 1959).

In our own investigations, we found that the coupling of 2-cyanophenylboronic acid esters allows almost quantitative conversion of the 1-p-halobenzyl-1H-imidazole substrate to the coupling product, if the reaction conditions are adjusted accordingly. However, the corresponding boronates are only obtained in moderate yields, since their preparation from boronic acid requires heating and several crystallization steps to obtain the desired ester in a defined composition. This fact is of importance with regard to the considerable costs of o-cyanophenylboronic acid.

Recently, aryltrifluoroboronates have been reported as an alternative to arylboronic acids as substrates for the Suzuki cross-coupling reactions to obtain substituted biaryl compounds with aryl halides [a) Molander, G. A. et al., J. Org. Chem. 2003, 6E, 4302. b) Molander, G. A. et al., Org. Lett. 2002, 4, 1867]. However, it was unknown whether and to what extent a cyano substituent might interfere with this reaction. Since it is well known that hydrolysis of cyano groups results in the formation of the corresponding carboxylic acid, one would have expected at least the partial formation of undesired side products in aqueous media (Advanced Organic Chemistry, J. March, 4th Edition, page 888).

We have now surprisingly found that novel (2-cyanophenyl)-trifluoroboronates can be very efficiently prepared from o-cyanophenylboronic acid or acid derivatives. Such procedure allows using also 2-cyanophenylboronic acid of technical grade as a starting material. Such compounds are useful intermediates for the preparation of sartan derivatives.

SUMMARY OF THE INVENTION

Thus, the present invention provides a process for the preparation of sartan derivatives of formula (I) or pharmaceutically acceptable salts thereof, and particularly losartan, olmesartan medoxomil, candesartan cilexetil, and irbesartan:

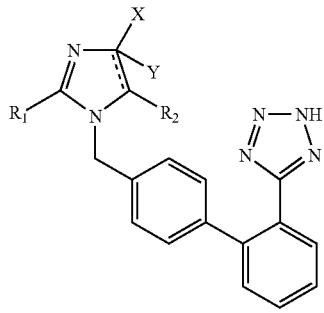

(I)

wherein ----- can be a single bond or a double bond and wherein if ----- is a double bond, then Y does not exist, $R_1$ is
  $C_2$-$C_7$ straight-chain or branched alkyl, preferably straight $C_3$-$C_5$ alkyl, most preferably n-propyl or n-butyl,
  $C_2$-$C_7$ straight-chain or branched alkoxy, preferably straight $C_2$-$C_5$ alkoxy, most preferably n-ethoxy, or
  $C_3$-$C_9$ cycloalkyl, such as cyclopropyl, cyclobutyl, cyclopentyl, cyclohexyl, cycloheptyl, cyclooctyl and cyclononyl, most preferably cyclopentyl, $R_2$ is hydroxymethyl, formyl, or an optionally substituted carboxyl group, wherein the substituent may be a straight or branched $C_1$-$C_{10}$ alkyl group, a $C_3$-$C_8$ cycloalkyl group, a $C_6$-$C_{10}$ aryl group or a $C_7$-$C_{13}$ aralkyl group, or $R_2$ is a group of formula

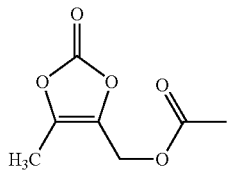

X is H, Cl or

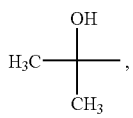

or X and $R_2$, taken together with the double bond of the imidazole ring, form a 6-membered aromatic ring which can be substituted by a carboxyl group, which may be further substituted with a straight or branched $C_1$-$C_{10}$ alkyl group, a $C_3$-$C_8$ cycloalkyl group, a $C_6$-$C_{10}$ aryl group, a $C_7$-$C_{13}$ aralkyl group, or a group of the formula

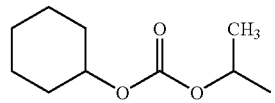

and if ----- is a single bond, then $R_1$ is $C_2$-$C_7$ straight-chain or branched alkyl, preferably straight $C_3$-$C_5$ alkyl, most preferably n-butyl, $R_2$ is =O and X and Y form a $C_4$-$C_7$-cycloalkyl group, preferably a $C_5$-$C_6$ cycloalkyl group, most preferably a cyclopentyl group, comprising the steps of:

reacting a 2-cyanophenylboronic acid derivative, selected from (a) a compound represented by formula (III)

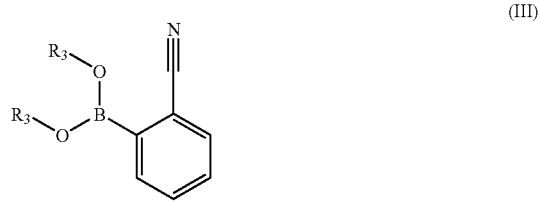

(III)

wherein $R_3$ independently stands for H or an unsubstituted or substituted $C_1$-$C_4$ alkyl or $C_6$-$C_{10}$ aryl group or wherein two $R_3$ groups form a 1,2-phenylene group (the term "independently" is used herein to indicate that the $R_3$ groups can be identical or different, e.g. all $R_3$ groups may be substituted alkyl groups or one of them may be a substituted alkyl group and the other may be an unsubstituted alkyl group or an aryl group, etc.; the same applies in the following), or an alkali salt thereof, wherein the alkali salt is preferably sodium or potassium, most preferably potassium, (b) a compound represented by formula (IV)

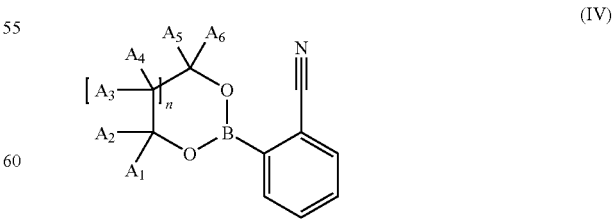

(IV)

wherein n is 0 or 1; and $A_1$-$A_6$ are independently H or an optionally substituted $C_1$-$C_4$ alkyl, $C_3$-$C_8$ cycloalkyl or $C_{6\text{-}10}$ aryl group or (c) a compound represented by formula (V),

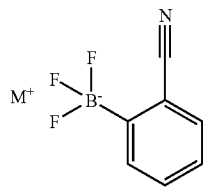

(V)

wherein M is an alkali metal or an $NR_4R_5R_6R_7$ group wherein $R_4$-$R_7$ are independently H or an unsubstituted or substituted $C_1$-$C_{18}$ alkyl group, in a cross-coupling reaction with an p-halobenzyl-1H-imidazole derivative of formula (VI),

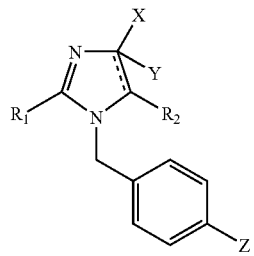

(VI)

wherein ⋯X, Y, $R_1$ and $R_2$ are as defined above, and Z is I, Br or Cl, in the presence of a transition metal catalyst and an inorganic or organic base to form a substituted biphenyl imidazole compound of formula (II)

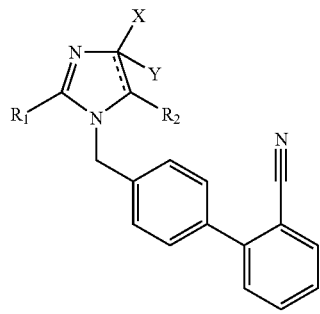

(II)

wherein ⋯X, Y, $R_1$ and $R_2$ are as defined above, converting the compound of formula (II) into the corresponding 2-tetrazole derivative to obtain a sartan derivative of formula (I), preferably losartan, olmesartan and the medoxomil ester thereof, candesartan and the cilexetil ester thereof, and irbesartan, and optionally, converting said sartan derivative into one of its pharmaceutically acceptable salts or esters, for example losartan into losartan potassium.

In a further aspect, the invention provides a process as described above which, as a preceding step further comprises the synthesis of a compound according to formula (V)

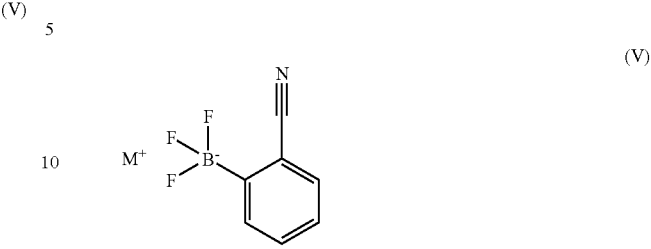

(V)

wherein M is an alkali metal, preferably potassium, or a $NR_4R_5R_6R_7$ group wherein $R_4$-$R_7$ are independently H, $C_1$-$C_{18}$ unsubstituted or substituted alkyl, preferably tetra-n-butylammonium, comprising the steps of lithiation or magnesiation of a 2-halobenzonitrile wherein halo means I, Br, Cl and reacting the resulting product with a borate ester of formula $B(OR)_3$, wherein R is $C_1$-$C_4$ alkyl, and reacting the resulting compound with an inorganic or organic hydrogendifluoride or combination of an inorganic or organic base with hydrofluoric acid or with potassium hydrogendifluoride, optionally followed by exchanging the potassium cation with a different cation by reaction with an organic or inorganic base to obtain a compound of formula (V).

In a further aspect, the invention provides a process as described above which, as a preceding step further comprises the synthesis of a compound according to formula (V), wherein M is defined as above, comprising the step of transmetallation of a 2-halobenzonitrile wherein halo means I, Br, Cl, with a zinc or copper salt, reacting the resulting product with tetra-fluoroborate or $BF_3$ and an inorganic or organic base to obtain a compound of formula (V).

Alternatively, 2-cyanophenylboronic acid can be reacted with an inorganic or organic hydrogendifluoride or a combination of an inorganic or organic base with hydrofluoric acid or with potassium hydrogenfluoride, to obtain a compound of formula (V).

In a further step of any of the above processes the potassium cation can be exchanged with another inorganic or organic cation by reaction with an organic or inorganic base.

The invention also provides novel intermediates of formula (II) and (V) as described above and their use in the preparation of sartan derivatives, particularly losartan, olmesartan medoxomil, candesartan cilexetil, and irbesartan.

DETAILED DESCRIPTION

The various reaction steps and intermediates that can be used for the preparation of important intermediates in the preparation of sartan derivatives such as losartan, olmesartan medoxomil, candesartan cilexetil, and irbesartan, are now described in greater detail with reference to preferred embodiments.

In one preferred embodiment the present invention provides a process for the preparation of certain sartan derivatives of formula (II),

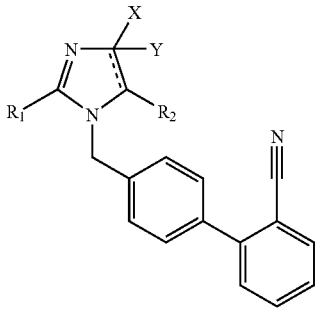

wherein ----- can be a single bond or a double bond and wherein if ----- is a double bond, then Y does not exist; $R_1$, $R_2$, X and Y are as defined above; $R_1$ is preferably n-propyl, n-butyl or n-ethoxy, $R_2$ is preferably hydroxymethyl, or

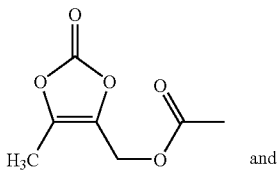

and

X is preferably Cl,

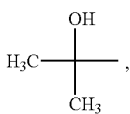

or X and $R_2$, taken together with the double bond of the imidazole ring, form a 6-membered aromatic ring which is preferably substituted by a group of the formula

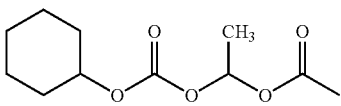

and if ----- is a single bond, then $R_1$ is preferably n-butyl, $R_2$ is =O and X and Y form preferably a cyclopentyl group, by reacting a 1H-imidazole derivative of formula (VI),

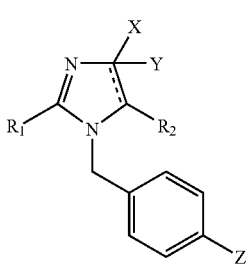

wherein -----X, Y, $R_1$ and $R_2$ are as defined above, and Z is preferably Br, and a 2-cyanophenylboronic acid derivative of formula (III) or an alkali metal salt thereof, (IV) and (V) in the presence of a transition metal catalyst and a base in an organic or aqueous solvent or solvent mixture to obtain a compound of formula (II).

The novel (2-cyanophenyl)-trifluoroboronate of formula (V) exhibits a surprisingly high stability and is therefore suitable for a Suzuki cross-coupling reaction under aqueous conditions.

If, in one of the above definitions, a group may be "substituted", this means that it may contain 1-3 halogen atoms, preferably Cl or F, or one, two or three $C_1$-$C_3$-alkoxy groups, $C_1$-$C_3$ alkyl groups or $C_6$-$C_{10}$ aryl groups.

To obtain losartan, the reaction is preferably carried out by reacting 2-n-butyl-4-chloro-1-p-bromobenzyl-1H-imidazole derivative of formula (V) ($R_1$=n-butyl, $R_2$=$CH_2OH$, X=Cl, Y=Br) with a 2-cyanophenylboronic acid derivative in the presence of a metal catalyst and a base, such as an inorganic base, for example sodium or potassium carbonate, $K_3PO_4.nH_2O$, $KF.2H_2O$ and alkali metal alkoxides or organic bases such as triethylamine or diisopropylethylamine. The reaction is conducted in an organic solvent such as dimethylformamide, dimethylacetamide, NMP, dimethylsulfoxide, acetonitrile, $C_1$-$C_4$ alcohols such as methanol, ethanol, n- and iso-propanol, or n-butanol, toluene, tetrahydrofurane, dioxane, DME and their combinations or mixtures thereof with water. Diisopropylamine is particularly preferred as a base; another preferred solvent is 95% aqueous ethanol; diisopropylamine in industrial ethanol is a preferred base/solvent combination. Even more preferred are anhydrous alcohols, especially anhydrous ethanol.

Likewise, to obtain candesartan cilexetil, the reaction is preferably carried out by reacting (±)1-[[(cyclohexyloxy)-carbonyl]oxy]ethyl-1-(4-bromobenzyl)-2-ethoxy-1H-benzimidazole-7-carboxylate with potassium (2-cyanophenyl)-tetrafluoroboronate in the presence of a metal catalyst and a base, such as an inorganic base, for example sodium or potassium carbonate, $K_3PO_4.nH_2O$, $KF.2H_2O$ and alkali metal alkoxides or organic bases such as triethylamine or diisopropylethylamine. The reaction is conducted in an organic solvent such as dimethylformamide, dimethylacetamide, NMP, dimethylsulfoxide, acetonitrile, $C_1$-$C_4$ alcohols such as methanol, ethanol, n- and iso-propanol, or n-butanol, toluene, tetrahydrofurane, dioxane, DME and their combinations or mixtures thereof with water. Diisopropylamine is particularly preferred as a base; another preferred solvent is 95% aqueous ethanol; diisopropylamine in industrial ethanol is a preferred base/solvent combination. Even more preferred are anhydrous alcohols, especially anhydrous ethanol.

Likewise, to obtain irbesartan, the reaction is preferably carried out by reacting 1-(4-bromobenzyl)-2-n-butyl-4-spirocyclopentane-2-imidazoline-5-one with potassium (2-cyanophenyl)-tetrafluoroboronate in the presence of a metal catalyst and a base, such as an inorganic base, for example sodium or potassium carbonate, $K_3PO_4.nH_2O$, $KF.2H_2O$ and alkali metal alkoxides or organic bases such as triethylamine or diisopropylethylamine. The reaction is conducted in an organic solvent such as dimethylformamide, dimethylacetamide, NMP, dimethylsulfoxide, acetonitrile, $C_1$-$C_4$ alcohols such as methanol, ethanol, n- and iso-propanol, or n-butanol, toluene, tetrahydrofurane, dioxane, DME and their combinations or mixtures thereof with water. Diisopropylamine is particularly preferred as a base; another preferred solvent is 95% aqueous ethanol; diisopropylamine in industrial ethanol is a preferred base/solvent combination. Even more preferred are anhydrous alcohols, especially anhydrous ethanol.

Likewise, to obtain olmesartan, the reaction is preferably carried out by reacting ethyl-4-(1-hydroxy-1-methylethyl)-2-propyl-1-(4-bromobenzyl)imidazole-5-carboxylate with potassium (2-cyanophenyl)-tetrafluoroboronate in the presence of a metal catalyst and a base, such as an inorganic base, for example sodium or potassium carbonate, $K_3PO_4.nH2O$, $KF.2H_2O$ and alkali metal alkoxides or organic bases such as triethylamine or diisopropylethylamine. The reaction is conducted in an organic solvent such as dimethylformamide, dimethylacetamide, NMP, dimethylsulfoxide, acetonitrile, $C_1$-$C_4$ alcohols such as methanol, ethanol, n- and iso-propanol, or n-butanol, toluene, tetrahydrofurane, dioxane, DME and their combinations or mixtures thereof with water. Diisopropylamine is particularly preferred as a base; another preferred solvent is 95% aqueous ethanol; diisopropylamine in industrial ethanol is a preferred base/solvent combination. Even more preferred are anhydrous alcohols, especially anhydrous ethanol. The coupling product of this reaction can then be converted into the ethyl ester of olmesartan, preferably by cycloaddition, and the ethyl ester can be transesterified to obtain another ester of olmesartan, or can be hydrolyzed to give olmesartan. In the alternative, the coupling product may be hydrolyzed before the cycloaddition step is carried out.

The coupling reaction is carried out at about 25° C. to 180° C., preferably at about 50 to 130° C., most preferably at about 70 to 110° C.

The metal catalyst used in the reaction is a complex of nickel, palladium, or platinum, preferably a palladium complex such as e.g. bis(acetonitrile)palladium dichloride, tetrakis(triphenylphosphine)palladium, bis(dibenzylideneacetone)palladium, tris(dibenzylideneacetone)dipalladium, a phosphinated palladium II complex selected from the group consisting of: bis(triphenylphosphine)palladium chloride, bis(triphenylphosphine)palladium bromide, bis(triphenylphosphine)palladium acetate, bis(triisopropylphosphite)palladium chloride, bis(triisopropylphosphite)palladium bromide, bis(triisopropylphosphite)palladium acetate, [1,2-bis(diphenylphosphino)ethane]palladium chloride, [1,2-bis(diphenylphosphino)ethane]palladium bromide, [1, 2 bis(diphenylphosphino)ethane]palladium acetate, [1,3-bis(diphenylphosphino)propane]palladium chloride, [1,3-bis(diphenylphosphino)propane]palladium bromide, [1,3-bis(diphenylphosphino)propane]palladium acetate, [1,4-bis(diphenylphosphino)butane]palladium chloride, [1,4-bis(diphenylphosphino)butane]palladium bromide, [1,4-bis(diphenylphosphino)butane]palladium acetate and [1,1'-bis(diphenylphosphino)ferrocene]palladium chloride. The active catalyst may be prepared in advance or generated in the reaction mixture in situ.

The active catalyst can also be prepared from a Pd (II) salt such as palladium chloride, palladium bromide or palladium acetate with phosphine, typically triphenylphosphine or tritolylphosphine under the action of a reducing agents such as dialkylzinc, alkylzinc halide, dialkylmagnesium, alkylmagnesium halide, trialkylaluminum, dialkylaluminum hydride, sodium borohydride, hydrazine, or arylboronic acid in a suitable solvent. In a preferred embodiment diethylzinc is used as reducing agent.

Under certain circumstances the reduction step can be replaced so that the palladium precursor is reduced and the active catalyst is formed in the reaction mixture.

The reaction can be performed using a catalyst with or without phosphine ligands. However, in a preferred embodiment phosphine is used as a ligand in a ratio of Pd:Phosphine 1:4, as it increases the stability of the catalytically active palladium complex.

The metal atom, ion or metal precursor may be supported or not. Supports may be of organic or inorganic nature. In further embodiments, the support will not form part of the metal precursor and suitable supports include silicas, aluminas, zeolites, polyethyleneglycols, polystyrenes, polyesters, polyamides, peptides and the like. Specific examples of Pd supported metals include Pd/C, $Pd/SiO_2$, $Pd/CaCO_3$, $Pd/BaCO_3$, Pd/aluminate, Pd/aluminum oxide, Pd/polystyrene. Any of the metals listed above can replace Pd in this list, e.g., Ni/C, etc.

In general, the solvents for the reaction can be selected from a variety of known solvents. Illustrative solvents that can be utilized either singly or in combinations are benzene, toluene, ethyl ether, tetrahydrofurane, dioxane, NMP, acetonitrile, dimethylformamide, dimethylacetamide, dimethylsulfoxide, ethanol, methanol, propanol, isopropyl alcohol, water, 2-methyltetrahydrofuran or diethoxymethane. A preferable solvent is aqueous ethanol, tetrahydrofurane or toluene, even more preferred is anhydrous ethanol. It is suitable to use degassed solvents.

There are a variety of bases that can be generally used for effecting the reaction(s). Illustrative examples are organic tertiary non-nucleophilic bases such as triethylamine or diisopropylethylamine, inorganic bases such as potassium carbonate, sodium carbonate, cesium carbonate, cesium fluoride, potassium fluoride, potassium phosphate, potassium hydroxide, sodium hydroxide, or the alkoxides of these alkali metals. When an inorganic base insoluble in the organic solvent is used, dissolution in water may be necessary; the use of a phase-transfer catalyst such as tetra-n-butylammonium bromide or crown ether also facilitate the reaction. Bases which are soluble in organic solvents such as tetra-n-butylammonium carbonate or tetra-n-butylammonium hydroxide, benzyltrimethylammonium carbonate, benzyltrimethylammonium methyl carbonate, benzyltrimethylammonium methoxide or benzyltrimethylammonium hydroxide, or other basic tetraalkylammonium compounds are particularly useful in certain cases. The base soluble in an organic solvent may be prepared in advance or generated in the reaction mixture. For example, the preparation of benzyltrimethylammonium carbonate can be achieved by reacting a benzyltrimethylammonium hydroxide solution with ammonium carbonate.

The base is preferably used in the process of the invention in an amount of about 1 to about 1000 mol %, more preferably from about 50 to about 500 mol %, most preferably from about 100 to about 400 mol %, in particular from about 150 to about 300 mol %, based on the boronic acid derivative.

After a reaction time expediently of 2 hours to 24 hours, the resulting compound of the formula (II) can be isolated from the reaction mixture in a manner known to those skilled in the art, but preferentially by precipitation from the reaction medium by addition of water.

Expediently, the molar ratio of (III), (IV) or (V), respectively, to the derivative of formula (VI) is between 1 and 1.5, particularly if the compound of formula (VI) is 2-n-butyl-1-p-halobenzyl-1H-imidazole.

A particularly preferred embodiment of the present invention involves the conditions of 1% $Pd(OAc)_2$+4% $P(o-C_6H_4CH_3)$ or 2% $Pd(OAc)_2$+8% $PPh_3$, 4 eq. $i-Pr_2NEt$ in 95% aqueous ethanol in the cross-coupling reaction of potassium (2-cyanophenyl)-trifluoroboronate with 2-n-butyl-1-p-bromobenzyl-4-chloro-1H-imidazole-5-ylmethanol or a similar sartan precursor compound of formula (VI) as defined above. Under these preferred reaction conditions the 4'-(2-butyl-4-chloro-5-hydroxymethyl-1H-imidazole-1-yl)-1,1'-biphenyl-2-carbonitrile derivative of formula (II) is obtained in particularly high yields. However, the use of other palladium catalysts (ligandless or with other phosphine ligands), bases and solvents also results in the formation of the desired substrate of formula (VI) in considerable yields.

The novel (2-cyanophenyl)-trifluoroboronate derivatives of formula (V) are prepared by reaction of 2-cyanophenylboronic acid with an inorganic or organic hydrogendifluoride, or a combination of an inorganic or organic base with hydrofluoric acid, or with potassium hydrogendifluoride followed by exchange of the potassium cation with another inorganic or organic one with an organic or inorganic base. The base is selected from an organic tertiary non-nucleophilic base, wherein the organic tertiary non-nucleophilic base is selected from the group consisting of triethylamine or diisopropylethylamine, or an inorganic base, wherein the inorganic base is selected from potassium carbonate, sodium carbonate, cesium carbonate, potassium phosphate, potassium fluoride, potassium hydrogenfluoride, potassium alkoxide or sodium alkoxide, and a base soluble in an organic solvent, wherein the base is selected from a group consisting of tetra-n-butylammonium carbonate, tetra-n-butylammonium hydroxide, benzyltrimethylammonium carbonate, benzyltrimethylammonium methyl carbonate, benzyltrimethylammonium methoxide, or benzyltrimethylammonium hydroxide.

Alternatively, the (2-cyanophenyl)-trifluoroboronate derivatives of formula (V) are prepared by lithiation or magnesiation of 2-halobenzonitrile wherein halo means I, Br, Cl and reacting the resulting product with borate ester of formula $B(OR)_3$ wherein R is a $C_1$-$C_4$ alkyl group and reacting the resulting compound with an inorganic or organic hydrogendifluoride or combination of inorganic or organic base with hydrofluoric acid or with potassium hydrogendifluoride, optionally followed by exchanging the potassium cation with different cation by reaction with an organic or inorganic base to obtain a compound of formula (V). The preparation of the intermediates is carried out by methods well known to those skilled in the art. Thus, e.g. the o-lithiation was disclosed in U.S. Pat. No. 5,039,814. However, the reaction steps in the synthesis must be compatible with the functional groups on the imidazole moiety and other parts of the molecule.

In a second alternative, the (2-cyanophenyl)-trifluoroboronate derivatives of formula (V) are prepared by transmetallation of 2-halobenzonitrile wherein halo means I, Br, Cl, with a zinc or copper salt, reacting the resulting product with tetrafluoroborate or $BF_3$ and an inorganic or organic base to obtain a compound of formula (V). The resulting 2-cyanophenylboronic acid is further reacted with an inorganic or organic hydrogendifluoride or a combination of an inorganic or organic base with hydrofluoric acid or with potassium hydrogenfluoride. In a further step the potassium cation can be exchanged with another inorganic or organic cation by reaction with an organic or inorganic base.

The conversion of compounds of formula (II) into compounds of formula (I) can be performed by any method known by one skilled in the art.

The reaction of the cyano croup with an azide, especially with sodium azide, is especially preferred. Likewise, the sartan derivative of formula (I) may be converted in one of its pharmaceutically acceptable salts by any known method. A preferred example may be the reaction with potassium or sodium hydroxide.

In a preferred embodiment the sartan derivatives of formula (I) are converted into the corresponding potassium salts. In the case of irbesartan and candesartan, the coupling product of formula (I) can be further converted to irbesartan and candesartan cilexetil, respectively, and purified by converting them into a corresponding tetrazole-protected derivative thereof, e.g. a trityl derivative thereof, followed by a deprotection step to obtain the desired sartan derivative of formula (I). In the case of olmesartan, the coupling product of formula (I) can be converted into a tetrazole-protected olmesartan ethyl ester, followed by trans-esterification to give a tetrazole-protected olmesartan medoxomil ester, followed by a deprotection step to obtain olmesartan medoxomil ester. The protecting group in each of these cases is preferably a trityl group.

Another aspect of the invention is a process for the preparation of a compound of formula (VI) as defined above, characterized in that an imidazole derivative of formula (VII)

(VII)

wherein X, Y, $R_1$ and $R_2$ are as defined above, is reacted with a 4-halobenzylhalogenide, wherein halogen is Cl, Br or I, preferably Br, in the presence of a base under reflux. In a preferred embodiment 2-n-butyl-4-spirocyclopentane-2-imidazoline-5-one hydrochloride is reacted with 4-bromobenzylbromide in the presence of tetrabutylammonium bromide and potassium hydroxide.

The invention is illustrated by the following examples. The examples do not intend to limit the scope of this invention as defined in the claims below.

EXAMPLES

Example 1

Preparation of potassium (2-cyanophenyl)-trifluoroboronate 2.50 g of 2-cyanophenylboronic acid was dissolved in 100 mL MeOH and a solution of 4.40 g $KHF_2$ (3.30 eq.) in 50 mL $H_2O$ was added. The reaction mixture was heated to reflux and the solvent was evaporated in vacuo. A white residue was extracted 3 times with each 50 mL of warm dried acetone. The solution was concentrated to a volume of about 50 mL and 400 mL of diethyl ether was added slowly. Precipitated crystals of potassium (2-cyanophenyl)-trifluoroboronate were filtered off, washed with ether and dried. Yield: 2.90 g (82%) of a white crystalline solid (M.p. 169-171° C.). $^1$H NMR (300 MHz, d$_6$-DMSO, δ): 7.52 d (1H), 7.50 d (1H), 7.39 dd (1H), 7.23 ddd (1H).

Example 2

A) Preparation of 4'-(2-butyl-4-chloro-5-hydroxymethyl-1H-imidazole-1-yl)-1,1'-biphenyl-2-carbonitrile 0.50 g (1.40 mmol) of potassium (2-cyanophenyl)-trifluoroboronate, 0.35 g (1.68 mmol, 1.2 eq.) of 2-n-butyl-1-p-bromobenzyl-4-chloro-1H-imidazole-5-ylmethanol (assay: 93%), 3.00 mg (0.014 mmol, 0.01 eq.) of palladium acetate, 17 mg (0.056 mmol, 0.04 eq.) of tri-o-tolylphosphine were given into a dried flask equipped with reflux condenser. The flask was capped with a septum and filled with argon in three cycles. 10 mL of 95% aqueous ethanol, saturated with argon and 0.50 mL (4 eq.) of diisopropyethylamine saturated with argon were added to the flask via a syringe. The reaction mixture was heated and refluxed for 12 hours. Color changes from yellowish (palladium acetate) via red-brown (active palladium species) up to precipitation of inactive palladium black were observed. The precipitation of palladium black occurred after 6 hours. Then, the reaction mixture was opened to the atmosphere and the solvent was evaporated under vacuo. 1.00 g of silica gel was added to the residue, moistened with 5.00 mL of ethyl acetate and the solvent was evaporated. The reaction mixture deposited on silica gel was transferred on the top of a short silica gel column (10 g of silica gel with ethyl acetate-hexane 1:1 (v/v)) and the column was eluted with ethyl acetate-hexane 1:1 (v/v). Evaporation of the solvent afforded 0.50 g (94%, assay: 90%) of a crude yellowish solid product. The obtained material was crystallized from ethyl acetate-hexane providing 0.45 g (84%) of 4'-(2-butyl-4-chloro-5-hydroxymethyl-1H-imidazole-1-yl)-1,1'-biphenyl-2-carbonitrile in form of a white crystalline solid (m.p. 154.1-155.5° C.). $^1$H NMR (300 MHz, CDCl$_3$, δ): 7.77 dd (1H), 7.65 ddd (1H), 7.53 d (2H), 7.42-7.50 m (2H), 7.12 d (2H), 5.29 s (2H), 4.53 d (2H), 2.60 t (2H), 1.68 m (2H), 1.36 m (2H), 0.89 t (3H)

B) Preparation of 4'-(2-butyl-4-chloro-5-hydroxymethyl-1H-imidazole-1-yl)-1,1'-biphenyl-2-carbonitrile Analogous to example 2A, but instead of 3 mg of palladium acetate and 23 mg of tri-c-tolylphosphine, 6.00 mg (0.03 mmol, 0.02 eq.) of palladium acetate and 29 mg (0.11 mmol, 0.08 eq.) of triphenylphosphine were used.

C) Preparation of 4'-(2-butyl-4-chloro-5-hydroxymethyl-1H-imidazole-1-yl)-1,1'-biphenyl-2-carbonitrile 8.00 g (22.5 mmol) 2-n-butyl-1-p-bromobenzyl-4-chloro-1H-imidazole-5-ylmethanol, 5.64 g (27.0 mmol, 1.2 eq.) potassium (2-cyanophenyl)-trifluoroboronate, 50.0 mg (0.23 mmol, 0.01 eq.) palladium acetate, 273 mg (0.90 mmol, 0.04 eq.) tri-o-tolylphosphine were given into a dried flask equipped with a reflux condenser. The flask was capped with a septum and purged with argon in three cycles. 150 mL of 95% aqueous ethanol, saturated with argon and 15.3 mL (90.0 mmol, 4 eq.) diisopropylethylamine saturated with argon were added to the flask via syringe. The reaction mixture was heated to reflux and stirred at this temperature for 18 hours. Then, the reaction mixture was opened to atmosphere and the solvent was evaporated under vacuo. The reaction mixture was purified by chromatography (ethyl acetate-hexanes 1:1). The solvent was removed and the residue was extracted with warm cyclohexane (to remove residual phosphine) and then crystallized from ethyl acetate-hexanes (1:1), to obtain the first portion of product. The mother liquor was purified by chromatography and crystallized to afford the second portion of product. The product was obtained in 89% (7.54 g) yield as a white crystalline powder with a m.p. of 154-156° C.

$^1$H NMR benzyl methylene signal 96.5 mol. % (5.29 ppm) (isomeric compound 1.2 mol. % (5.25 ppm) and 2-n-butyl-1-p-bromobenzyl-4-chloro-1H-imidazole-5-ylmethanol 2.3 mol. % (5.22 ppm); HPLC (phenyl reverse-phase column, 40% acetonitrile aq.) 254 nm: 98.2% (11.95 min)+polar impurity 1.8% (3.64 min); 235 nm: 97.7% (11.96 min)+polar impurity 2.3% (3.70 min).

0.60 g (7%) 4'-(2-butyl-4-chloro-5-hydroxymethyl-1H-imidazole-1-yl)-1,1'-biphenyl-2-carbonitrile as off-white crystalline powder, m.p. 152-154° C.; Assay: $^1$H NMR 93.5% (isomeric compound 2.8 mol. % (5.25 ppm) and 2-n-butyl-1-p-bromobenzyl-4-chloro-1H-imidazole-5-ylmethanol 3.7 mol. % (5.22 ppm); HPLC (phenyl reverse-phase column, 40% acetonitrile aq.) 235 nm: 95.6% (12.00 min)+polar impurity 4.4% (3.69 min).

Total yield: 8.14 g (96%).

Example 3

Preparation of 4'-(2-butyl-4-chloro-5-hydroxymethyl-1H-imidazole-1-yl)-1,1'-biphenyl-2-carbonitrile Analogous to example 2B, but the catalyst was prepared separately. Tri-o-tolylphosphine (17.0 mg) was dissolved in THF (20 mL) and the solution was degassed by vacuum/nitrogen purges (3 times). Palladium acetate (3.00 mg, 0.25 mmol) was added and the solution was degassed again (3 times). The resulting solution was warmed to 60° C. for 30 min, then cooled to 25° C. and used for the reaction.

Example 4

Preparation of 4'-(2-butyl-4-chloro-5-hydroxymethyl-1H-imidazole-1-yl)-1,1'-biphenyl-2-carbonitrile Analogous to example 2, but the catalyst was separately prepared. To a mixture of palladium chloride (50.0 mg) and triphenylphosphine (0.70 g) was added anhydrous THF (20 mL). The heterogeneous solution was degassed by vacuum/nitrogen purges (3 times) and then triisopropylphosphite (0.30 mL) was added in one portion. The mixture was maintained at room temperature with stirring until the entire palladium chloride was dissolved and a homogeneous solution was obtained.

Example 5

Preparation of 4'-(2-butyl-4-chloro-5-formyl-1H-imidazole-1-yl)-1,1'-biphenyl-2-carbonitrile Analogous to example 2B, but instead of 2-n-butyl-1-p-bromobenzyl-4-chloro-1H-imidazole-5-ylmethanol 2-n-butyl-1-p-bromobenzyl-4-chloro-1H-imidazole-5-carbaldehyde was used.

Example 6

Preparation of tetra-n-butylammonium (2-cyanophenyl)-trifluoroboronate

A flask with 2.00 g of 2-bromobenzonitrile (11.0 mmol) capped with a septum was flushed with argon and 30 mL of dry degassed THF was added. The solution was cooled to −94° C. and 10 mL of 1.60 M n-butyllithium solution in hexane (16.0 mmol, 1.50 eq.) was slowly added within 10 min. The obtained solution was stirred for 20 min at this temperature. 33.0 ml of 1.50 M solution of zinc chloride (22.0 mmol, 2.00 eq.) were added to the reaction mixture and stirred for 20 min. The solution consisting of 7.20 g (22.0 mol, 2.00 eq.) tetra-n-butylammonium tetrafluoroborate in 20 mL THF was slowly added and the reaction mixture was stirred for 1 hour at −94° C. The reaction was allowed to warm up to room temperature overnight. Then it was opened to the air, and the solvent was removed in vacuo. The residue was washed with diethyl ether and extracted three times with 50 mL of warm dry acetone. The obtained solution was concentrated to about 50 mL and 400 mL of diethyl ether was added. The precipitate was filtered off, washed with ether and dried. 2.50 g (56%) of tetra-n-butylammonium (2-cyanophenyl)-trifluoroboronate as a white crystalline solid was obtained. Assay: $^1$H NMR>98%.

Example 7

Preparation of potassium (2-cyanophenyl)-trifluoroboronate

A flask with 2.00 g of 2-bromobenzonitrile (11.0 mmol) capped with septum was flushed with argon and 30 mL of dry degassed THF was added. The solution was cooled to −94° C. and 10 mL of 1.60 M n-butyllithium solution in hexane (16.0 mmol, 1.5 eq.) was added slowly within 10 min. The obtained solution was stirred for 20 min at this temperature. 5.00 mL of trimethyl borate (45 mol, 4.0 eq.) was slowly added and the reaction mixture was stirred for 1 hour still at −94° C. The reaction was allowed to warm up to room temperature overnight. Then it was opened to the air, and the solvent was removed in vacuo. 100 mL of methanol and a solution comprising of 2.10 g of KHF$_2$ in 50 mL of water were added. The resulting mixture was heated to reflux and the solvents were evaporated. Residue was washed with diethyl ether and extracted three times with 50 mL of dried, warm acetone. The solution was concentrated to a volume of about 50 mL and 400 mL of diethyl ether was added. The precipitate was filtered off, washed with ether and dried. 1.58 g (69%) of potassium (2-cyanophenyl)-trifluoroboronate as white crystalline solid was obtained.

Assay: $^1$H NMR>98%.

Example 8

Preparation of Losartan 0.381 g (1.00 mmol) of 4'-(2-butyl-4-chloro-5-hydroxymethyl-1H-imidazole-1-yl)-1,1'-biphenyl-2-carbonitrile and 0.82 ml (3.00 mmol) of tributyltin azide were suspended in 6 ml of toluene and heated to reflux temperature. The reaction mixture was stirred at this temperature for 96 h. After the reaction was completed, the suspension was cooled to room temperature and 4 ml of 2M KOH were added. The phases were separated and the water phase was acidified to a pH of approximately 3. The precipitated product was filtered and dried. We isolated 0.33 g of the product.

$^1$H NMR (300 MHz, DMSO-d$_6$, δ): 7.63-7.72 m (2H), 7.50-7.60 m (2H), 7.05 m (4H), 5.25 s (2H), 4.33 bs (2H), 2.50 t (2H), 1.45 m (2H), 1.23 m (2H), 0.80 t (3H), OH and NH are exchanged.

Example 9

Preparation of Candesartan Cilexetil

A) Preparation of (±)1-[[(cyclohexyloxy)carbonyl]oxy]ethyl-2-ethoxy-1-[(2'-cyanobiphenyl-4-yl)-methyl]-1H-benzimidazole-7-carboxylate 0.06 g (0.26 mmol) of potassium (2-cyanophenyl)-tetrafluoroboronate, 0.11 g (0.2 mmol) of (±)1-[[(cyclohexyloxy)carbonyl]oxy]ethyl 1-(4-bromobenzyl)-2-ethoxy-1H-benzimidazole-7-carboxylate, 1 mg (0.004 mmol) of palladium acetate, 2 mg (0.007 mmol) of tri-o-tolylphosphine were given into the dried flask equipped with reflux condenser. The flask was capped with septum and filled with argon in three cycles. 1.2 mL of ethanol, saturated with argon and 0.06 mL of diisoproplyethylamine saturated with argon were added to the flask via a syringe. Reaction mixture was heated and refluxed for 20 hours. Then, the reaction mixture was opened to the atmosphere, cooled, filtered and the solvent was evaporated under vacuo. To the residue 5 ml of isopropyl acetate and 5 ml of water were added. The mixture was stirred and then separated. The organic phase was washed twice with 5 ml of water, dried over Na$_2$SO$_4$ and evaporated to give 150 mg of oily residue.

$^1$H NMR (300 MHz, DMSO, δ): 7.9 m (1H), 7.75 m (2H), 7.45-7.60 m (5H), 7.22 m (1H), 7.10 d (2H), 6.80 m (1H), 5.60 d (2H), 4.46-4.68 m (3H), 1.15-1.80 m (16H).

B) Preparation of (±)-1-[[(cyclohexyloxy) carbonyl]oxy]ethyl-2-ethoxy-1-[[2'-(1H-tetrazol-5-yl)[1,1'-biphenyl]-4-yl]methyl]-1H-benzimidazole-7-carboxylate The mixture of 0.057 g (0.1 mmol) (±)1-[[(cyclohexyloxy)carbonyl]oxy]ethyl-2-ethoxy-1-[(2'-cyanobiphenyl-4-yl)-methyl]-1H-benimidazole-7-carboxylate, 2 ml toluene, 0.054 ml (0.3 mmol) tributyltin chloride and 20 mg (0.3 mmol) NaN$_3$, were heated under reflux temperature for 72 h. The reaction mixture was cooled and concentred. The residue was purified by column chromatography on silica gel to give 70 mg of candesartan cilexetil.

Example 10

A) Preparation of 1-(4-bromobenzyl)-2-n-butyl-4-spirocyclopentane-2-imidazoline-5-one The mixture of 50 ml acetonitrile, 2.76 (12 mmol) of 2-n-butyl-4-spirocyclopentane-2-imidazoline-5-one hydrochloride, 2.48 g (10 mmol) of 4-bromobenzylbromide, 1.39 g (4.3 mmol) of tetrabutylammonium bromide and 3.67 g (65.5 mmol) KOH was heated under reflux for 4 h. The suspension was cooled and concentrated under reduced pressure. To the residue 50 ml of water was added and the mixture was neutralized by addition of about 31 ml of 1M HCl to pH 6. The product was extracted with 80 ml of CH$_2$Cl$_2$ and the organic phase was washed twice with water, dried over Na$_2$SO$_4$, filtered and evaporated. 2.67 g of the oily product was obtained.

The sample of the product for analytical purpose was obtained by purification of crude product using flash chromatography (hexane:ethyl acetate:triethylamine 2:1:0.1, v:v:v).

The preparation of 1-(4-bromobenzyl)-2-n-butyl-4-spirocyclopentane-2-imidazoline-5-one was performed according to the process disclosed in WO 2006/073376.

$^1$H NMR (300 MHz, DMSO, δ): 7.55 d (2H), 7.11 d (2H), 4.65 s (2H), 3.3 t (2H), 1.58-1.94 m (8H), 1.46 m (2H), 1.24 m (2H), 0.79 t (3H).

B1) Preparation of Irbesartan 0.712 g (3.12 mmol) of potassium (2-cyanophenyl)-tetrafluoroboronate, 0.92 g (2.53 mmol) of 1-(4-bromobenzyl)-2-n-butyl-4-spirocyclopentane-2-imidazoline-5-one, 12 mg (0.05 mmol) of palladium acetate, 22 mg (0.07 mmol) of tri-o-tolylphosphine were given into the dried flask equipped with reflux condenser. The flask was capped with septum and filled with argon in three cycles. 14 mL of ethanol, saturated with argon and 0.72 mL of diisopropyethylamine saturated with argon were added to the flask via a syringe. Reaction mixture was heated and refluxed for 20 hours. Then, the reaction mixture was cooled, filtered and the solvent was evaporated under vacuo. To the residue 20 ml of xylene and 21 ml of 0.05 M HCl were added. The mixture was stirred and then separated. The organic phase was washed twice with 5 ml of water, dried over Na$_2$SO$_4$ and evaporated to give 10 ml of the solution of the product.

To this solution of 1.3 ml (7.2 mmol) tributyltin chloride and 468 mg (7.2 mmol) NaN$_3$ were added and heated under reflux temperature for 42 h. The mixture was cooled and then 16 ml of 0.2 M NaOH were added. After stirring, the phases were separated and water phase extracted by 20 ml of tert-butyl methyl ether. Water phase was acidified to pH 4-5 and cooled. The precipitated product was filtered and 0.84 g of irbesartan were isolated.

B2) Preparation of Irbesartan 0.074 g (0.5 mmol) of 2-cyanophenylboronic acid, 0.225 g (0.6 mmol) of 1-(4-bromobenzyl)-2-n-butyl-4-spirocyclopentane-2-imidazoline-5-one, 3 mg (0.01 mmol) of palladium acetate, 6 mg (0.02 mmol) of tri-o-tolylphosphine were given into the dried flask equipped with reflux condenser. The flask was capped with septum and filled with argon in three cycles. 3.6 mL of ethanol, saturated with argon and 0.18 mL of diisopropyethylamine saturated with argon were added to the flask via a syringe. Reaction mixture was heated and refluxed for 22 hours. Then, the reaction mixture was opened to the atmosphere, cooled, filtered and the solvent was evaporated under reduced pressure. To the residue 5 ml of xylene and 5.3 ml of 0.05 M HCl were added. The mixture was stirred and then separated. The organic phase was washed twice with 5 ml of water, dried over Na$_2$SO$_4$ an evaporated to give 3 ml of the solution of the cyano product.

To this solution of 0.33 g (1 mmol) tributyltin azide were added and heated under reflux temperature for 42 h. Xylene was evaporated and 5 ml of CH$_2$Cl$_2$ and 5 ml of water were added. The phases were separated and then to organic phase 10 ml of 0.2 M NaOH were added. After stirring, the phases were separated and water phase extracted by 10 ml of tert-butyl methyl ether. Water phase was acidified to pH 4-5 and cooled and precipitated product was filtered. 0.13 g of irbesartan were isolated.

Example 11

Preparation of Olmesartan

A) Preparation of ethyl-4-(1-hydroxy-1-methylethyl)-2-propyl-1-(4-bromobenzyl)imidazole-5-carboxylate (VII)

The mixture of 240 ml acetonitrile, 20.7 g (150 mmol) of K$_2$CO$_3$, 18 g (75 mmol) of ethyl-4-(1-hydroxy-1-methylethyl)-2-propylimidazole-5-carboxylate and 20.4 g (81.6 mmol) of 4-bromobenzylbromide was heated under reflux temperature for 7 h. The suspension is cooled, filtered and concentrated under reduced pressure to approximately ⅓ of the starting volume and stirred at about 0° C. for 1 h. The precipitate is filtered and dried at 35° C. for 1 h and afterwards suspended in 218 ml of water. The mixture is stirred for 2 h, filtered and dried again. 21.56 g of the crude product were isolated. Crude product was recrystallized from acetonitrile (87%, 55% of the synthesis)

T=84-85° C.

IR (main peaks):3371, 2961, 1666, 1529, 1404, 1176, 1009, 780, $^1$H NMR (300 MHz, DMSO, δ): 7.54 d (2H), 6.90 d (2H), 5.42 s (2H), 5.39 s (1H), 4.14 q (2H), 2.60 t (2H), 1.59 m (2H), 1.50 s (6H), 1.07 t (3H), 0.87 t (3H).

B) Preparation of ethyl-4-(1-hydroxy-1-methylethyl)-2-propyl-1-[(2'-cyanobiphenyl-4-yl)-methyl]-imidazole-5-carboxylate 0.89 g (3.9 mmol) of potassium (2-cyanophenyl)-tetrafluoroboronate, 1.35 g (3.3 mmol) of ethyl 4-(1-hydroxy-1-methylethyl)-2-propyl-1-(4-bromobenzyl)imidazole-5-carboxylate, 15 mg (0.07 mmol) of palladium acetate, 30 mg (0.1 mmol) of tri-o-tolylphosphine were given into the dried flask equipped with reflux condenser. The flask was capped with a septum and filled with argon in three cycles. 18 mL of ethanol, saturated with argon and 0.9 mL of diisopropylethylamine saturated with argon were added to the flask via a syringe. Reaction mixture was heated and refluxed for 20 hours. Then, the reaction mixture was cooled, filtered and the solvent was evaporated under vacuo. To the residue 40 ml of isopropyl acetate and 42 ml of 0.05 M HCl were added. The mixture was stirred and then separated. The organic phase was washed twice with 40 ml of water, dried over Na$_2$SO$_4$ an evaporated to give 1.76 g of oily residue. The sample of the product for analytical purpose was purified using flash chromatography (MPh: hexane:ethyl acetate 1:1; v:v).

$^1$H NMR (300 MHz, DMSO, δ): 7.93 ddd (1H), 7.78 ddd (1H) 7.61-7.54 m (4H), 7.11 d (2H), 5.55 s (2H), 5.42 s (1H), 4.16 q (2H), 2.65 t (2H), 1.63 m (2H), 1.49 s (6H), 1.07 t (3H), 0.90 t (3H).

C) Preparation of ethyl-4-(1-hydroxy-1-methylethyl)-2-propyl-1-[[2'-(1H-tetrazol-5-yl) [1,1'-biphenyl]-4-yl]methyl]-imidazole-5-carboxylate The mixture of 0.56 g (0.8 mmol) ethyl-4-(1-hydroxy-1-methylethyl)-2-propyl-1-[(2'-cyanobiphenyl-4-yl)-methyl]-imidazole-5-carboxylate, 3 ml toluene, 0.65 ml (2.1 mmol) tributyltin chloride and 0.13 mg (2 mmol) NaN$_3$, were heated under reflux for 42 h. The reaction mixture was evaporated under reduced pressure and the residue was dissolved in 5.5 ml of 2.5 M HCl in ethanol. The solution was stirred for 18 h and then concentrated. The residue was triturated in diisopropyl ether to give 0.51 g of the title compound as hydrochloride salt.

T=100-103° C.

$^1$H NMR (300 MHz, CD$_3$OD, δ): 6.9-7.8 m (8H), 5.70 s (2H), 4.30 q (2H), 3.00 t (2H), 1.70 s (6H), 1.57 m (2H), 1.24 t (3H), 0.97 t (3H).

In a further step, ethyl-4-(1-hydroxy-1-methylethyl)-2-propyl-1-[[2'-(1H-tetrazol-5-yl)[1,1-biphenyl]-4-yl]methyl]-imidazole-5-carboxylate can hydrolyzed to obtain olmesartan.

The invention claimed is:

1. A process for the preparation of a sartan derivative of formula (I)

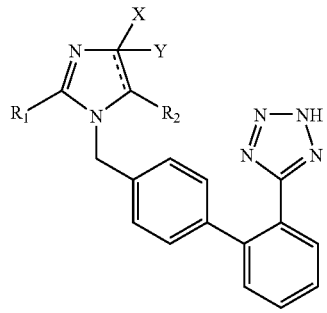

(I)

wherein ----- can be a single bond or a double bond and wherein if ----- is a double bond, then Y does not exist, R$_1$ is C$_2$-C$_7$ straight-chain or branched alkyl, C$_2$-C$_7$ straight-chain or branched alkoxy or C$_3$-C$_9$ cycloalkyl, R$_2$ is hydroxymethyl, formyl, or an optionally substituted carboxyl group, wherein the substituent may be a straight or branched C$_1$-C$_{10}$ alkyl group, a C$_3$-C$_8$ cycloalkyl group, a C$_6$-C$_{10}$ aryl group or a C$_7$-C$_{13}$ aralkyl group, or R$_2$ is a group of formula

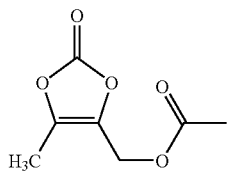

X is H, Cl,

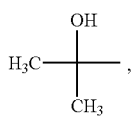

or X and R$_2$, taken together with the double bond of the imidazole ring, form a 6-membered aromatic ring which can be substituted by a carboxyl group which may be further substituted with a straight or branched C$_1$-C$_{10}$ alkyl group, a C$_3$-C$_8$ cycloalkyl group, a C$_6$-C$_{10}$ aryl group, a C$_7$-C$_{13}$ aralkyl group, or a group of the formula

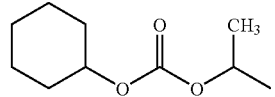

and if ----- is a single bond, then

R$_1$ is C$_2$-C$_7$ straight-chain or branched alkyl,

R$_2$ is =O and X and Y form a C$_4$-C$_7$ cycloalkyl group, or a pharmaceutically acceptable salt thereof, comprising the steps of:

reacting 2-cyanophenylboronic acid or a derivative thereof, wherein said 2-cyanophenylboronic acid or derivative is selected from (a) a compound represented by formula (III)

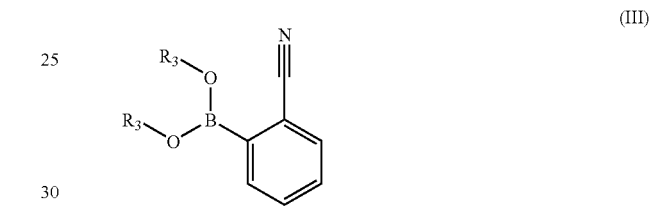

(III)

wherein the R$_3$ groups independently stand for H or an unsubstituted or substituted C$_1$-C$_4$ alkyl or a C$_6$-C$_{10}$ aryl group or wherein two R$_3$ groups form a 1,2-phenylene group, or an alkali metal salt thereof, (b) a compound represented by formula (IV)

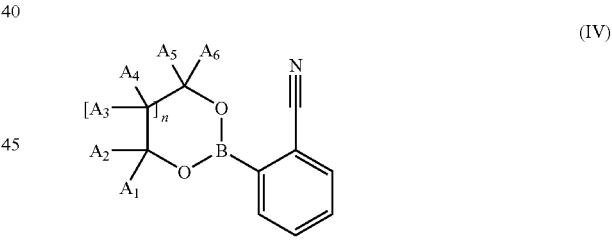

(IV)

wherein n is 0 or 1; and A$_1$-A$_6$ are independently H or an optionally substituted C$_1$-C$_4$ alkyl group, C$_3$-C$_8$ cycloalkyl group or C$_6$-C$_{10}$ aryl group or (c) a compound represented by formula (V)

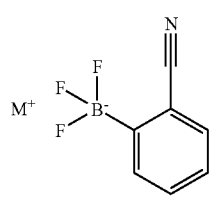

(V)

wherein M is an alkali metal or an NR$_4$R$_5$R$_6$R$_7$ group wherein R$_4$-R$_7$ are independently H or an unsubstituted or substituted $C_1$-$C_{18}$ alkyl group in a cross-coupling reaction with a p-halobenzyl-1H-imidazole derivative of formula (VI),

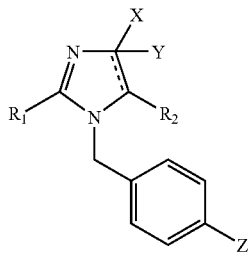

wherein ≡≡≡, X, Y, $R_1$ and $R_2$ are as defined above, and Z is I, Br or Cl, in the presence of a solvent, a transition metal catalyst and an inorganic or organic base to form a substituted biphenyl imidazole compound of formula (II)

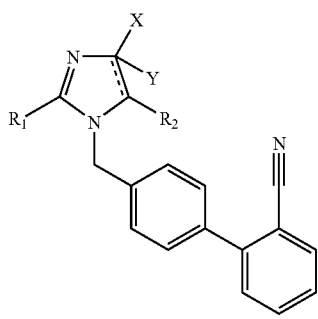

wherein ≡≡≡, X, Y, $R_1$ and $R_2$ are as defined above,
converting the compound of formula (II) into the corresponding 2-tetrazole derivative to obtain a sartan derivative of formula (I) and, optionally,
converting the sartan derivative into one of its pharmaceutically acceptable salts or esters.

2. A process according to claim 1, wherein said sartan derivative is selected from losartan, olmesartan, candesartan and irbesartan, and pharmaceutically acceptable salts and esters thereof.

3. A process according to claim 1, wherein said pharmaceutically acceptable salt is losartan potassium.

4. A process according to claim 1, wherein said pharmaceutically acceptable ester is candesartan cilexetil.

5. A process according to claim 1, wherein said pharmaceutically acceptable ester is olmesartan medoxomil.

6. A process according to claim 1, characterized in that the inorganic or organic base is selected from potassium carbonate, sodium carbonate, cesium carbonate, cesium fluoride, triethylamine or diisopropylethylamine.

7. A process according to claim 1 characterized in that the solvent is selected from dimethylformamide, tetrahydrofurane, toluene, toluene-methanol, methanol or ethanol, or a mixture thereof with water.

8. A process according to claim 1 characterized in that the transition metal catalyst is a palladium complex selected from tetrakis(triphenylphosphine)palladium (0), tetrakis(tri-o-tolylphosphine)palladium (0), bis[1,1'-bis(diphenylphosphino)ferrocene]palladium (0) or a phosphinated palladium (II) complex.

9. A process according to claim 1 comprising the steps of:
a) mixing a compound of formula (III), (IV) or (V), a compound of formula (VI), and inorganic or organic base and transition metal catalyst precursors,
b) adding a solvent to form a mixture,
c) heating the mixture to reflux for 3-12 hours to produce a compound of formula (II),
d) purifying the reaction mixture containing a compound of formula (II), and
e) converting the compound of formula (II) into a compound of formula (I).

10. A process according to claim 1 further comprising the steps of:
lithiation or magnesiation of a 2-halobenzonitrile wherein halo means I, Br, Cl and reacting the resulting product with a borate ester of formula $B(OR)_3$, wherein is R is $C_1$-$C_4$ alkyl and
reacting the resulting compound with an inorganic or a organic hydrogen difluoride or a combination of an inorganic or organic base with hydrofluoric acid or with potassium hydrogen difluoride, optionally followed by exchanging the potassium cation with a different cation by reaction with an organic or inorganic base to obtain a compound of formula (V)

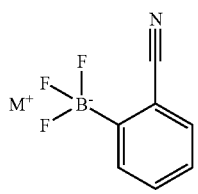

wherein M is an alkali metal or an $NR_4R_5R_6R_7$ group wherein $R_4$-$R_7$ are independently H or an unsubstituted or substituted $C_1$-$C_{18}$ alkyl group as defined above.

11. A process according to claim 1 further comprising the step of:
transmetallation of a 2-halobenzonitrile, wherein halo means I, Br, Cl, with a zinc or copper salt,
reacting the resulting product with a tetrafluoroborate or $BF_3$ and an inorganic or organic base to obtain a compound of formula (V)

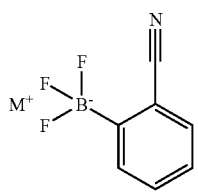

wherein M is an alkali metal or an $NR_4R_5R_6R_7$ group wherein $R_4$-$R_7$ are independently H or an unsubstituted or substituted $C_1$-$C_{18}$ alkyl group as defined above.

12. A process according to claim 1 further comprising the step of reacting 2-cyanophenylboronic acid with an inorganic or organic hydrogen difluoride or a combination of an inorganic or organic base with hydrofluoric acid or with potassium hydrogen difluoride to obtain a compound of formula (V).

13. A process according to claim 11 further comprising the step of exchanging the potassium cation with another inorganic or organic cation by reaction with an organic or inorganic base.

14. A process according to claim 1, wherein the compound of formula (VI) is prepared by reacting 2-n-butyl-4-spirocyclopentane-2-imidazoline-5-one hydrochloride with 4-bromobenzylbromide in the presence of tetrabutylammonium bromide and potassium hydroxide under reflux.

15. A process according to claim 12 further comprising the step of exchanging the potassium cation with another inorganic or organic cation by reaction with an organic or inorganic base.

* * * * *